United States Patent
Claizergues

(10) Patent No.: US 12,042,231 B2
(45) Date of Patent: Jul. 23, 2024

(54) PRE-OPERATIVE PLANNING OF BONE GRAFT TO BE HARVESTED FROM DONOR SITE

(71) Applicant: Howmedica Osteonics Corp., Mahwah, NJ (US)

(72) Inventor: Bertrand Claizergues, Montbonnot (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 85 days.

(21) Appl. No.: 17/632,146

(22) PCT Filed: Aug. 4, 2020

(86) PCT No.: PCT/US2020/044889
§ 371 (c)(1),
(2) Date: Feb. 1, 2022

(87) PCT Pub. No.: WO2021/026156
PCT Pub. Date: Feb. 11, 2021

(65) Prior Publication Data
US 2022/0265358 A1    Aug. 25, 2022

Related U.S. Application Data

(60) Provisional application No. 62/884,079, filed on Aug. 7, 2019.

(51) Int. Cl.
*A61B 34/10*        (2016.01)
*A61B 90/00*        (2016.01)
(Continued)

(52) U.S. Cl.
CPC .............. *A61B 34/10* (2016.02); *A61B 90/37* (2016.02); *G06T 7/50* (2017.01); *G06T 7/60* (2013.01);
(Continued)

(58) Field of Classification Search
CPC ... G06T 7/50; G06T 7/60; G06T 2207/30008; G16H 30/20; G16H 30/40; G16H 40/60;
(Continued)

(56) References Cited

U.S. PATENT DOCUMENTS

| 6,648,894 B2 | 11/2003 | Abdelgany et al. |
| 7,802,503 B2 | 9/2010 | Couvillion et al. |

(Continued)

FOREIGN PATENT DOCUMENTS

| EP | 2845547 A1 | 3/2015 |
| EP | 3395281 A1 | 10/2018 |

(Continued)

OTHER PUBLICATIONS

"Blueprint 3d Planning Software + PSI," Wright Medical Group, retrieved from https://www.wright.com/blueprint-3d-planning-psi-system on Oct. 15, 2020, 9 pp.

(Continued)

*Primary Examiner* — Wesner Sajous
(74) *Attorney, Agent, or Firm* — Shumaker & Sieffert, P.A.

(57) ABSTRACT

Techniques are described for bone graft selection in orthopedic surgery. Processing circuitry may determine a bone graft template for a bone graft to be connected to a first anatomical object, determine information indicative of placement of the bone graft template within a representation of a second anatomical object based on image data for one or more images of anatomical objects, and output the information indicative of the placement of the bone graft template within the representation of the second anatomical object.

24 Claims, 9 Drawing Sheets

(51) Int. Cl.

| | | |
|---|---|---|
| *G06F 3/048* | (2013.01) | |
| *G06T 7/50* | (2017.01) | |
| *G06T 7/60* | (2017.01) | |
| *G16H 30/20* | (2018.01) | |
| *G16H 30/40* | (2018.01) | |
| *G16H 40/67* | (2018.01) | |
| *G16H 50/50* | (2018.01) | |

(52) U.S. Cl.
CPC .............. *G16H 30/20* (2018.01); *G16H 30/40* (2018.01); *G16H 40/67* (2018.01); *G16H 50/50* (2018.01); *A61B 2034/105* (2016.02); *A61B 2034/107* (2016.02); *A61B 2034/108* (2016.02); *G06T 2207/30008* (2013.01)

(58) Field of Classification Search
CPC ........ G16H 40/67; G16H 70/60; G16H 50/50; G16H 50/70; A61B 34/10; A61B 34/20; A61B 90/37; A61B 2090/365; A61B 2090/502; A61B 2090/372; A61B 90/90; A61B 90/361; A61B 90/39; A61B 90/94; A61B 17/15; A61B 17/1635; A61B 17/1637; A61B 17/1775; A61B 17/1684; A61B 17/1659; A61B 17/1604; A61B 2034/105; A61B 2034/108; A61B 2034/107; A61B 2017/00123; A61B 2017/0015; A61B 2017/00017; A61B 2505/05; A61B 2562/0219; A61B 2034/2055; A61B 2090/081; A61B 2090/0807; A61B 2090/3762; A61B 2090/267; A61B 2090/062; A61B 2090/374; A61F 2/4606; A61F 2002/4658; G06F 3/0482; G06F 3/04815; G06F 18/2163; G06F 30/10

See application file for complete search history.

(56) References Cited

U.S. PATENT DOCUMENTS

| | | | |
|---|---|---|---|
| 8,971,606 B2 | 3/2015 | Chaoui et al. | |
| 11,033,300 B2* | 6/2021 | Pavlovskaia | G16H 30/40 |
| 11,045,227 B2* | 6/2021 | Park | G06T 7/0012 |
| 11,439,469 B2* | 9/2022 | Poltaretskyi | G06T 7/55 |
| 11,478,310 B2* | 10/2022 | Poltaretskyi | A61B 5/681 |
| 11,571,263 B2* | 2/2023 | Moore | A61B 17/1604 |
| 11,645,531 B2* | 5/2023 | Moore | G06N 3/08 |
| | | | 345/419 |
| 11,657,287 B2* | 5/2023 | Poltaretskyi | G16H 40/67 |
| | | | 345/419 |
| 2008/0183297 A1 | 7/2008 | Booileau et al. | |
| 2012/0010710 A1 | 1/2012 | Frigg | |
| 2012/0253350 A1 | 10/2012 | Anthony et al. | |
| 2017/0340390 A1* | 11/2017 | Harbison | G06T 19/20 |
| 2018/0233222 A1 | 8/2018 | Daley et al. | |
| 2019/0380792 A1 | 12/2019 | Poltaretskyi et al. | |
| 2022/0039868 A1 | 2/2022 | Chaoui et al. | |
| 2022/0054195 A1 | 2/2022 | Chaoui et al. | |
| 2022/0059212 A1* | 2/2022 | Chaoui | G06N 3/045 |
| 2022/0059213 A1 | 2/2022 | Chaoui et al. | |
| 2022/0148167 A1 | 5/2022 | Poltaretskyi et al. | |
| 2022/0148168 A1 | 5/2022 | Poltaretskyi et al. | |
| 2022/0156924 A1 | 5/2022 | Poltaretskyi et al. | |
| 2022/0156942 A1 | 5/2022 | Chaoui et al. | |

FOREIGN PATENT DOCUMENTS

| | | |
|---|---|---|
| WO | 2016007936 A2 | 1/2016 |
| WO | 2016191725 A1 | 12/2016 |
| WO | 2018187088 A1 | 10/2018 |
| WO | 2020123701 A1 | 6/2020 |
| WO | 2020123705 A1 | 6/2020 |
| WO | 2020123706 A1 | 6/2020 |
| WO | 2020123709 A1 | 6/2020 |
| WO | 2020205245 A1 | 10/2020 |
| WO | 2020205247 A1 | 10/2020 |
| WO | 2020205248 A1 | 10/2020 |
| WO | 2020205249 A1 | 10/2020 |

OTHER PUBLICATIONS

"HoloLens 2," Microsoft Hololens, retrieved from https://www.microsoft.com/en-us/hololens, on Oct. 15, 2020, 5 pp.
BIO-RSA, "Surgical Technique," Tornier, Jul. 2010, 20 pp.
Boissonnat, J.D., "Shape Reconstruction from Planar Cross Sections," Computer Vision, Graphics, and Image Processing, vol. 44, No. 1, Oct. 1988, 29 pp.
International Search Report and Written Opinion of International Application No. PCT/US2020/044889, dated Nov. 4, 2020, 14 pp.
Marker et al., "Contour-Based Surface Reconstruction using Implicit Curve Fitting, and Distance Field Filtering and Interpolation," vol. Graphics, Jan. 2006, 9 pp.
Nguyen et al., "A new segmentation method for MRI images of the shoulder joint," Fourth Canadian Conference on Computer and Robot Vision (CRV'07), May 2007, 8 pp.
Norris et al., "Management of Glenoid Bone Defects in Revision Shoulder Arthroplasty," Techniques in Shoulder & Elbow Surgery, vol. 8, No. 1, Mar. 2007, 10 pp.
Wright Medical, "BluePrint Video-Wright Medical Announces the Acquisition of IMASCAP SAS", accessed from www.imascap.com/wp-content/uploads/2017/12/blueprintvid.mp4, Dec. 14, 2017, 9 pp.
Wright, "BIO-RSA Bony Increased Offset—Reversed Shoulder Arthroplasty," Tornier, CAW-2150, Feb. 12, 2016, 20 pp.
Wright, "BluePrint, 3d Planning + PSI," User Manual V2.1, Tornier, CAW-8754, Nov. 2017, 18 pp.

* cited by examiner

PRE-OPERATIVE PLANNING OF BONE GRAFT TO BE HARVESTED FROM DONOR SITE

This application is a national stage application under 35 U.S.C. § 371 of PCT Application No. PCT/US2020/044889, filed Aug. 4, 2020, which claims the benefit of U.S. Provisional Application No. 62/884,079 filed Aug. 7, 2019. The entire contents of each of PCT Application No. PCT/US2020/044889 and U.S. Provisional Application No. 62/884,079 are incorporated herein by reference in their entirety.

BACKGROUND

Surgical repair procedures involve repair and/or replacement of a damaged or diseased anatomical object. One example of surgical repair procedures is bone grafting where a surgeon harvests bone, referred to as a bone graft, from a donor site for repairing damaged or diseased bone or for conditioning the damaged or diseased bone for implantation. The process of removing of the bone graft can negatively impact the donor site, such as causing bone fractures, cosmetic deformities, or injuring surrounding tissue, especially where the bone graft is larger than an amount of bone the donor site can donate without negative impact to the donor site. Also, after bone graft removal, the donor site may not have enough remaining bone to ensure proper fixation of an implant in the case an implant is needed at the donor site after bone graft harvesting procedure.

SUMMARY

This disclosure describes example techniques for providing preoperative planning for determining characteristics of a donor site for donating a bone graft. A computing device may determine a bone graft template of the bone graft (e.g., based on user input or determined based on image processing). A display device may display the bone graft template on a representation of the donor site, and a surgeon may determine whether the donor site includes sufficient bone to donate for the bone graft. In some examples, a computing device may be configured to compare the bone graft template to representation of the donor site, and output information indicative of whether the donor site includes sufficient bone to donate for the bone graft.

In this manner, the example techniques provide a technical solution for determining whether donor site is a proper donor site prior to a surgeon performing surgery. For instance, the example techniques provide for practical applications of preoperative planning utilizing image processing for determining whether to extract a bone graft from a donor site. In some examples, the disclosure describes example techniques to determine information indicative of a manner in which the bone graft is to be extracted (e.g., output visual information showing axis of cut, output visual information showing maximum depth of cut, output information indicative of type of tool to use, and the like). With the information indicative of the manner in which the bone graft is to be extracted, it may be possible for the computing device or the surgeon to determine a tools to use for the surgery including patient specific tools that can be viewed using augmented reality or mixed reality, and the like.

In one example, the disclosure describes a system for bone graft selection in orthopedic surgery, the system comprising a memory configured to store image data for one or more images of anatomical objects and processing circuitry. The processing circuitry is configured to determine a bone graft template for a bone graft to be connected to a first anatomical object, determine information indicative of placement of the bone graft template within a representation of a second anatomical object based on the image data, and output the information indicative of the placement of the bone graft template within the representation of the second anatomical object.

In one example, the disclosure describes a method for bone graft selection in orthopedic surgery, the method comprising determining a bone graft template for a bone graft to be connected to a first anatomical object, determining information indicative of placement of the bone graft template within a representation of a second anatomical object based on image data for one or more images of anatomical objects, and outputting the information indicative of the placement of the bone graft template within the representation of the second anatomical object.

In one example, the disclosure describes a system for bone graft selection in orthopedic surgery, the system comprising means for determining a bone graft template for a bone graft to be connected to a first anatomical object, means for determining information indicative of placement of the bone graft template within a representation of a second anatomical object based on image data for one or more images of anatomical objects, and means for outputting the information indicative of the placement of the bone graft template within the representation of the second anatomical object.

In one example, the disclosure describes a computer-readable storage medium storing instructions that when executed cause one or more processors to determine a bone graft template for a bone graft to be connected to a first anatomical object, determine information indicative of placement of the bone graft template within a representation of a second anatomical object based on image data for one or more images of anatomical objects, and output the information indicative of the placement of the bone graft template within the representation of the second anatomical object.

The details of various examples of the disclosure are set forth in the accompanying drawings and the description below. Various features, objects, and advantages will be apparent from the description, drawings, and claims.

DETAILED DESCRIPTION

Figure 1:
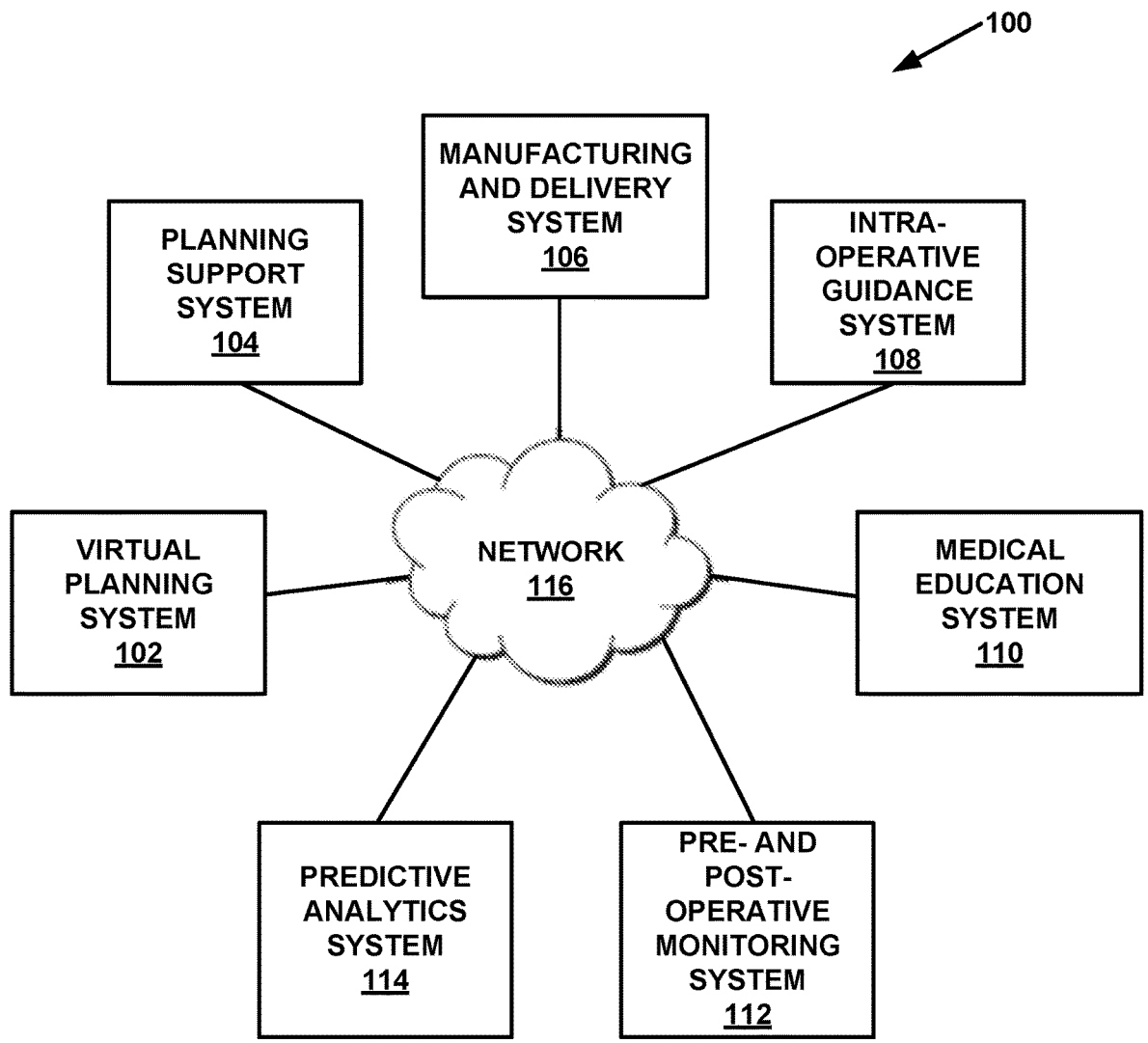
FIG. 1 is a block diagram of an orthopedic surgical system according to an example of this disclosure.

Orthopedic surgery can involve implanting one or more prosthetic devices to repair or replace a patient's damaged or diseased joint. Orthopedic surgery also includes grafting bone from a donor site to a target bone. The target bone may be a damaged or diseased bone or may be bone that is offset or augmented using the graft. Autografting refers to bone being taken from a donor site within the patient for grafting to the target bone within the same patient. The example techniques are described with respect to autografting but are applicable to other types of grafting as well (e.g., from a donor site not within the patient so called allograft, or from a synthetic source of material so called synthetic bone graft substitute). In some examples, the bone grafting may be used to augment or otherwise prepare the damaged or diseased bone for receiving the one or more prosthetic devices. In some examples, the bone graft is attached to a prosthetic device, and then the combined assembly (e.g., prosthetic device plus bone graft) are attached to the target bone.

Virtual surgical planning tools may use image data of the diseased or damaged joint to generate an accurate three-dimensional bone model that can be viewed and manipulated preoperatively by the surgeon. These tools can enhance surgical outcomes by allowing the surgeon to simulate the surgery, select or design an implant that more closely matches the contours of the patient's actual bone, and select or design surgical instruments and guide tools that are adapted specifically for repairing the bone of a particular patient.

Use of these planning tools typically results in generation of a preoperative surgical plan, complete with an implant and surgical instruments that are selected or manufactured for the individual patient. Oftentimes, once in the actual operating environment, the surgeon may desire to verify the preoperative surgical plan intraoperatively relative to the patient's actual bone. This verification may result in a determination that an adjustment to the preoperative surgical plan is needed, such as a different implant, a different positioning or orientation of the implant, and/or a different surgical guide for carrying out the surgical plan. In addition, a surgeon may want to view details of the preoperative surgical plan relative to the patient's real bone during the actual procedure in order to more efficiently and accurately position and orient the implant components. For example, the surgeon may want to obtain intra-operative visualization that provides guidance for positioning and orientation of implant components, guidance for preparation of bone or tissue to receive the implant components, guidance for reviewing the details of a procedure or procedural step, and/or guidance for selection of tools or implants and tracking of surgical procedure workflow.

As described above, for bone grafting, the surgeon extracts a bone graft from a donor site for grafting to the target bone. The surgeon may desire to determine characteristics of the donor site to determine whether the donor site is adequate for providing the bone graft. For example, the surgeon may desire to determine whether there is sufficient bone at the donor site, and as another example, whether the bone at the donor site is sufficiently dense. There may potentially be some negative impacts if there is insufficient bone at the donor site and/or if the bone at donor site is not sufficiently dense. For instance, there is potentially an increase in the probability of fracture at the donor site, there may be cosmetic deformities, and there may be damage to surrounding tissue at the donor site because the bone at the donor site is insufficient to properly support the tissue.

In accordance with the example techniques described in this disclosure, a computing device may generate information indicative of whether a donor site is suitable for being a donor for a bone graft. The surgeon may utilize the generated information to determine preoperatively whether to extract bone from the donor site. The surgeon may also utilize the generated information intraoperatively to confirm that the donor site is suitable, and as described in more detail, possibly utilize the generated information intraoperatively for surgical guidance.

For example, processing circuitry (e.g., processing circuitry of one or more computing devices) may be configured to determine a bone graft template for a bone graft to be connected to a first anatomical object (e.g., target bone). Bone graft template refers to a representation of size and shape of the bone graft that is to be extracted. The bone graft template may be a graphical representation that can be displayed. The bone graft template may be represented by shape equations that define a particular size and shape, or points within particular size and shape having assigned coordinates, as a few examples.

There may be various ways in which the processing circuitry determines the bone graft template. As one example, the processing circuitry may output for display image data showing the target bone, and the processing circuitry may receive input from the surgeon for what the bone graft template should look like. The processing circuitry may determine the bone graft template based on the received input. As another example, the processing circuitry may be configured to generate a pre-morbid construction of the target bone. The processing circuitry may determine a difference between the pre-morbid construction and the actual target bone to determine the bone graft template.

The processing circuitry may determine information indicative of placement of the bone graft template within a representation of a second anatomical object (e.g., donor site). For example, a memory may store image data for one or more images of anatomical objects. As one example, memory may store image data of computerized tomography (CT) scans of the patient. Part of the image data includes a representation of the donor site (e.g., images of the donor site). The processing circuitry may determine information indicative of how the bone graft template fits within the representation of the donor site based on the image data.

As one example, the surgeon may move (e.g., drag and place with a stylus) a displayed representation of the bone graft template within the representation of the donor site. In response to the movement of the bone graft template, the processing circuitry may determine information needed to move the representation of the bone graft template (e.g., information such as coordinates of where the bone graft template is to be displayed). The processing circuitry may then output information indicative of the placement of the bone graft template within the representation of the donor site (e.g., output graphical information used to render the bone graft template with the representation of the donor site).

As another example, the processing circuitry may be configured to utilize the points or shape equations of the bone graft template and the points in the representation of the donor site to determine how to place the bone graft template within the representation of the donor site. The processing circuitry may utilize certain criteria in determining information indicative of the placement such as information that defines boundaries within the donor site from where a bone graft can be extracted. For instance, the boundary may define certain configurations from which a bone graft can be extracted with comparative ease, where for other configurations of the bone graft template within the donor site, there may be complications in removing the bone graft (e.g., hard to access the bone graft). As another example, the boundary may define portions of the donor site where if the bone graft is removed from other portions there may be a possibility of cosmetic defect, injury, or susceptibility to injury. The processing circuitry may output the determined information (e.g., graphical information used to render the bone graft template within the representation of the donor site).

In some examples, in addition to generating information that can be used to determine whether a donor site is suitable for extracting a bone graft, the processing circuitry may be configured to generate information indicating whether the donor site is potentially suitable as a donor site for the bone graft (e.g., whether there is sufficient clearance, whether the bone graft extraction process can be performed with relative surgical ease, and the like). Also, in some examples, the processing circuitry may generate pre-operative planning information.

As one example, the processing circuitry may generate information indicative of a location from which the bone graft is to be extracted within the donor site (e.g., location that is to be cut for extracting the bone graft). In some examples, processing circuitry is configured to generate information indicative of an axis along which to the second anatomical object for extracting the bone graft. The processing circuitry may be configured to generate information indicative of a maximum depth at which to cut the second anatomical object for extracting the bone graft. As one example, the processing circuitry is configured to generate information indicative of a types of tool to utilize to cut the second anatomical object for extracting the bone graft.

In the techniques described in this disclosure, there may be various ways in which the surgeon may preoperatively view image content such as bone graft template, placement of bone graft template in donor site, and surgical guidance information. Also, in some examples, the surgeon may be able to view the bone graft template, placement of bone graft template in donor site, and surgical guidance information during the operation.

For example, the surgeon may use a mixed reality (MR) visualization system to assist with creation, implementation, verification, and/or modification of a surgical plan before and during a surgical procedure. Because MR, or in some instances virtual reality (VR), may be used to interact with the surgical plan, this disclosure may also refer to the surgical plan as a "virtual" surgical plan. Visualization tools other than or in addition to mixed reality visualization systems may be used in accordance with techniques of this disclosure.

A surgical plan, e.g., as generated by the BLUEPRINT™ system or another surgical planning platform, may include information defining a variety of features of a surgical procedure, such as features of particular surgical procedure steps to be performed on a patient by a surgeon according to the surgical plan including, for example, bone or tissue preparation steps and/or steps for selection, modification and/or placement of implant components. Such information may include, in various examples, dimensions, shapes, angles, surface contours, and/or orientations of implant components to be selected or modified by surgeons, dimensions, shapes, angles, surface contours and/or orientations to be defined in bone or tissue by the surgeon in bone or tissue preparation steps, and/or positions, axes, planes, angle and/or entry points defining placement of implant components by the surgeon relative to patient bone or tissue. Information such as dimensions, shapes, angles, surface contours, and/or orientations of anatomical features of the patient may be derived from imaging (e.g., x-ray, CT, MM, ultrasound or other images), direct observation, or other techniques.

In this disclosure, the term "mixed reality" (MR) refers to the presentation of virtual objects such that a user sees images that include both real, physical objects and virtual objects. Virtual objects may include text, 2-dimensional surfaces, 3-dimensional models, or other user-perceptible elements that are not actually present in the physical, real-world environment in which they are presented as coexisting. In addition, virtual objects described in various examples of this disclosure may include graphics, images, animations or videos, e.g., presented as 3D virtual objects or 2D virtual objects. Virtual objects may also be referred to as virtual elements. Such elements may or may not be analogs of real-world objects. In some examples, in mixed reality, a camera may capture images of the real world and modify the images to present virtual objects in the context of the real world. In such examples, the modified images may be displayed on a screen, which may be head-mounted, hand-held, or otherwise viewable by a user.

This type of mixed reality is increasingly common on smartphones, such as where a user can point a smartphone's camera at a sign written in a foreign language and see in the smartphone's screen a translation in the user's own language of the sign superimposed on the sign along with the rest of the scene captured by the camera. In some examples, in mixed reality, see-through (e.g., transparent) holographic lenses, which may be referred to as waveguides, may permit the user to view real-world objects, i.e., actual objects in a real-world environment, such as real anatomy, through the holographic lenses and also concurrently view virtual objects.

The Microsoft HOLOLENS™ headset, available from Microsoft Corporation of Redmond, Washington, is an example of a MR device that includes see-through holographic lenses, sometimes referred to as waveguides, that permit a user to view real-world objects through the lens and concurrently view projected 3D holographic objects. The Microsoft HOLOLENS™ headset, or similar waveguide-based visualization devices, are examples of an MR visualization device that may be used in accordance with some examples of this disclosure. Some holographic lenses may present holographic objects with some degree of transparency through see-through holographic lenses so that the user views real-world objects and virtual, holographic objects. In some examples, some holographic lenses may, at times, completely prevent the user from viewing real-world objects and instead may allow the user to view entirely virtual environments. The term mixed reality may also encompass scenarios where one or more users are able to perceive one or more virtual objects generated by holographic projection. In other words, "mixed reality" may encompass the case where a holographic projector generates holograms of elements that appear to a user to be present in the user's actual physical environment.

In some examples, in mixed reality, the positions of some or all presented virtual objects are related to positions of physical objects in the real world. For example, a virtual object may be tethered to a table in the real world, such that the user can see the virtual object when the user looks in the direction of the table but does not see the virtual object when the table is not in the user's field of view. In some examples, in mixed reality, the positions of some or all presented virtual objects are unrelated to positions of physical objects in the real world. For instance, a virtual item may always appear in the top right of the user's field of vision, regardless of where the user is looking.

Augmented reality (AR) is similar to MR in the presentation of both real-world and virtual elements, but AR generally refers to presentations that are mostly real, with a few virtual additions to "augment" the real-world presentation. For purposes of this disclosure, MR is considered to include AR. For example, in AR, parts of the user's physical environment that are in shadow can be selectively brightened without brightening other areas of the user's physical environment. This example is also an instance of MR in that the selectively-brightened areas may be considered virtual objects superimposed on the parts of the user's physical environment that are in shadow.

Furthermore, in this disclosure, the term "virtual reality" (VR) refers to an immersive artificial environment that a user experiences through sensory stimuli (such as sights and sounds) provided by a computer. Thus, in virtual reality, the user may not see any physical objects as they exist in the real world. Video games set in imaginary worlds are a common example of VR. The term "VR" also encompasses scenarios where the user is presented with a fully artificial environment in which some virtual object's locations are based on the locations of corresponding physical objects as they relate to the user. Walk-through VR attractions are examples of this type of VR.

The term "extended reality" (XR) is a term that encompasses a spectrum of user experiences that includes virtual reality, mixed reality, augmented reality, and other user experiences that involve the presentation of at least some perceptible elements as existing in the user's environment that are not present in the user's real-world environment. Thus, the term "extended reality" may be considered a genus for MR and VR. XR visualizations may be presented in any of the techniques for presenting mixed reality discussed elsewhere in this disclosure or presented using techniques for presenting VR, such as VR goggles.

FIG. 1 is a block diagram of an orthopedic surgical system 100 according to an example of this disclosure. Orthopedic surgical system 100 includes a set of subsystems. In the example of FIG. 1, the subsystems include a virtual planning system 102, a planning support system 104, a manufacturing and delivery system 106, an intraoperative guidance system 108, a medical education system 110, a monitoring system 112, a predictive analytics system 114, and a communications network 116. In other examples, orthopedic surgical system 100 may include more, fewer, or different subsystems. For example, orthopedic surgical system 100 may omit medical education system 110, monitor system 112, predictive analytics system 114, and/or other subsystems. In some examples, orthopedic surgical system 100 may be used for surgical tracking, in which case orthopedic surgical system 100 may be referred to as a surgical tracking system. In other cases, orthopedic surgical system 100 may be generally referred to as a medical device system.

Users of orthopedic surgical system 100 may use virtual planning system 102 to plan orthopedic surgeries. Users of orthopedic surgical system 100 may use planning support system 104 to review surgical plans generated using orthopedic surgical system 100. Manufacturing and delivery system 106 may assist with the manufacture and delivery of items needed to perform orthopedic surgeries. Intraoperative guidance system 108 provides guidance to assist users of orthopedic surgical system 100 in performing orthopedic surgeries. Medical education system 110 may assist with the education of users, such as healthcare professionals, patients, and other types of individuals. Pre- and postoperative monitoring system 112 may assist with monitoring patients before and after the patients undergo surgery. Predictive analytics system 114 may assist healthcare professionals with various types of predictions. For example, predictive analytics system 114 may apply artificial intelligence techniques to determine a classification of a condition of an orthopedic joint, e.g., a diagnosis, determine which type of surgery to perform on a patient and/or which type of implant to be used in the procedure, determine types of items that may be needed during the surgery, and so on.

The subsystems of orthopedic surgical system 100 (i.e., virtual planning system 102, planning support system 104, manufacturing and delivery system 106, intraoperative guidance system 108, medical education system 110, pre- and postoperative monitoring system 112, and predictive analytics system 114) may include various systems. The systems in the subsystems of orthopedic surgical system 100 may include various types of computing systems, computing devices, including server computers, personal computers, tablet computers, smartphones, display devices, Internet of Things (IoT) devices, visualization devices (e.g., mixed reality (MR) visualization devices, virtual reality (VR) visualization devices, holographic projectors, or other devices for presenting extended reality (XR) visualizations), surgical tools, and so on. A holographic projector, in some examples, may project a hologram for general viewing by multiple users or a single user without a headset, rather than viewing only by a user wearing a headset. For example, virtual planning system 102 may include a MR visualization device and one or more server devices, planning support system 104 may include one or more personal computers and one or more server devices, and so on. A computing system is a set of one or more computing systems configured to operate as a system. In some examples, one or more devices may be shared between the two or more of the subsystems of orthopedic surgical system 100. For instance, in the previous examples, virtual planning system 102 and planning support system 104 may include the same server devices.

In the example of FIG. 1, the devices included in the subsystems of orthopedic surgical system 100 may communicate using communication network 116. Communication network 116 may include various types of communication networks including one or more wide-area networks, such as the Internet, local area networks, and so on. In some examples, communication network 116 may include wired and/or wireless communication links.

Figure 2:
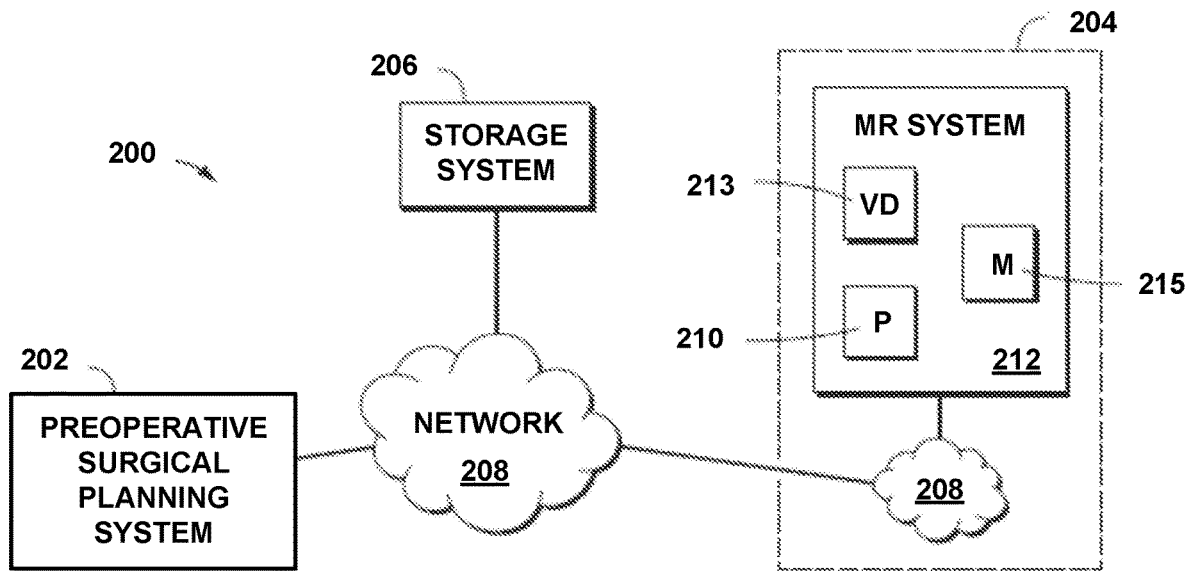
FIG. 2 is a block diagram of an orthopedic surgical system that includes a mixed reality (MR) system, according to an example of this disclosure.

Many variations of orthopedic surgical system 100 are possible in accordance with techniques of this disclosure. Such variations may include more or fewer subsystems than the version of orthopedic surgical system 100 shown in FIG. 1. For example, FIG. 2 is a block diagram of an orthopedic surgical system 200 that includes one or more mixed reality (MR) systems, according to an example of this disclosure. Orthopedic surgical system 200 may be used for creating, verifying, updating, modifying and/or implementing a surgical plan. In some examples, the surgical plan can be created preoperatively, such as by using a virtual surgical planning system (e.g., the BLUEPRINT™ system), and then verified, modified, updated, and viewed intraoperatively, e.g., using MR visualization of the surgical plan. In other examples, orthopedic surgical system 200 can be used to create the surgical plan immediately prior to surgery or intraoperatively, as needed. In some examples, orthopedic surgical system 200 may be used for surgical tracking, in which case orthopedic surgical system 200 may be referred to as a surgical tracking system. In other cases, orthopedic surgical system 200 may be generally referred to as a medical device system.

In the example of FIG. 2, orthopedic surgical system 200 includes a preoperative surgical planning system 202, a healthcare facility 204 (e.g., a surgical center or hospital), a storage system 206 and a network 208 that allows a user at healthcare facility 204 to access stored patient information, such as medical history, image data corresponding to the damaged joint or bone and various parameters corresponding to a surgical plan that has been created preoperatively (as examples). Preoperative surgical planning system 202 may be equivalent to virtual planning system 102 of FIG. 1 and, in some examples, may generally correspond to a virtual planning system similar or identical to the BLUEPRINT™ system.

In the example of FIG. 2, healthcare facility 204 includes a mixed reality (MR) system 212. In some examples of this disclosure, MR system 212 includes one or more processing device(s) (P) 210 to provide functionalities that will be described in further detail below. Processing device(s) 210 may also be referred to as processor(s) or processing circuitry. In addition, one or more users of MR system 212 (e.g., a surgeon, nurse, or other care provider) can use processing device(s) (P) 210 to generate a request for a particular surgical plan or other patient information that is transmitted to storage system 206 via network 208. In response, storage system 206 returns the requested patient information to MR system 212. In some examples, the users can use other processing device(s) to request and receive information, such as one or more processing devices that are part of MR system 212, but not part of any visualization device, or one or more processing devices that are part of a visualization device (e.g., visualization device 213) of MR system 212, or a combination of one or more processing devices that are part of MR system 212, but not part of any visualization device, and one or more processing devices that are part of a visualization device (e.g., visualization device 213) that is part of MR system 212.

In some examples, multiple users can simultaneously use MR system 212. For example, MR system 212 can be used in a spectator mode in which multiple users each use their own visualization devices so that the users can view the same information at the same time and from the same point of view. In some examples, MR system 212 may be used in a mode in which multiple users each use their own visualization devices so that the users can view the same information from different points of view.

In some examples, processing device(s) 210 can provide a user interface to display data and receive input from users at healthcare facility 204. Processing device(s) 210 may be configured to control visualization device 213 to present a user interface. Furthermore, processing device(s) 210 may be configured to control visualization device 213 to present virtual images, such as 3D virtual models, 2D images, and so on. Processing device(s) 210 can include a variety of different processing or computing devices, such as servers, desktop computers, laptop computers, tablets, mobile phones and other electronic computing devices, or processors within such devices. In some examples, one or more of processing device(s) 210 can be located remote from healthcare facility 204. In some examples, processing device(s) 210 reside within visualization device 213. In some examples, at least one of processing device(s) 210 is external to visualization device 213. In some examples, one or more processing device(s) 210 reside within visualization device 213 and one or more of processing device(s) 210 are external to visualization device 213.

In the example of FIG. 2, MR system 212 also includes one or more memory or storage device(s) (M) 215 for storing data and instructions of software that can be executed by processing device(s) 210. The instructions of software can correspond to the functionality of MR system 212 described herein. In some examples, the functionalities of a virtual surgical planning application, such as the BLUEPRINT™ system, can also be stored and executed by processing device(s) 210 in conjunction with memory storage device(s) (M) 215. For instance, memory or storage system 215 may be configured to store data corresponding to at least a portion of a virtual surgical plan. In some examples, storage system 206 may be configured to store data corresponding to at least a portion of a virtual surgical plan. In some examples, memory or storage device(s) (M) 215 reside within visualization device 213. In some examples, memory or storage device(s) (M) 215 are external to visualization device 213. In some examples, memory or storage device(s) (M) 215 include a combination of one or more memory or storage devices within visualization device 213 and one or more memory or storage devices external to the visualization device.

Network 208 may be equivalent to network 116. Network 208 can include one or more wide area networks, local area networks, and/or global networks (e.g., the Internet) that connect preoperative surgical planning system 202 and MR system 212 to storage system 206. Storage system 206 can include one or more databases that can contain patient information, medical information, patient image data, and parameters that define the surgical plans.

For example, medical images of the patient's target bone typically are generated preoperatively in preparation for an orthopedic surgical procedure. The medical images can include images of the relevant bone(s) taken along the sagittal plane and the coronal plane of the patient's body. The medical images can include X-ray images, magnetic resonance imaging (MM) images, computerized tomography (CT) images, ultrasound images, and/or any other type of 2D or 3D image that provides information about the relevant surgical area. Storage system 206 also can include data identifying the implant components selected for a particular patient (e.g., type, size, etc.), surgical guides selected for a particular patient, and details of the surgical procedure, such as entry points, cutting planes, drilling axes, reaming depths, etc. Storage system 206 can be a cloud-based storage system (as shown) or can be located at healthcare facility 204 or at the location of preoperative surgical planning system 202 or can be part of MR system 212 or visualization device (VD) 213, as examples.

MR system 212 can be used by a surgeon before (e.g., preoperatively) or during the surgical procedure (e.g., intra-operatively) to create, review, verify, update, modify and/or implement a surgical plan. In some examples, MR system 212 may also be used after the surgical procedure (e.g., postoperatively) to review the results of the surgical procedure, assess whether revisions are required, or perform other postoperative tasks. To that end, MR system 212 may include a visualization device 213 that may be worn by the surgeon and (as will be explained in further detail below) is operable to display a variety of types of information, including a 3D virtual image of the patient's diseased, damaged, or postsurgical joint and details of the surgical plan, such as a 3D virtual image of the prosthetic implant components selected for the surgical plan, 3D virtual images of entry points for positioning the prosthetic components, alignment axes and cutting planes for aligning cutting or reaming tools to shape the bone surfaces, or drilling tools to define one or more holes in the bone surfaces, in the surgical procedure to properly orient and position the prosthetic components, surgical guides and instruments and their placement on the damaged joint, and any other information that may be useful to the surgeon to implement the surgical plan. MR system 212 can generate images of this information that are perceptible to the user of the visualization device 213 before and/or during the surgical procedure.

In some examples, MR system 212 includes multiple visualization devices (e.g., multiple instances of visualization device 213) so that multiple users can simultaneously see the same images and share the same 3D scene. In some such examples, one of the visualization devices can be designated as the master device and the other visualization devices can be designated as observers or spectators. Any observer device can be re-designated as the master device at any time, as may be desired by the users of MR system 212.

In this way, FIG. 2 illustrates a surgical planning system that includes a preoperative surgical planning system 202 to generate a virtual surgical plan customized to repair an anatomy of interest of a particular patient. For example, the virtual surgical plan may include a plan for an orthopedic joint repair surgical procedure, such as one of a standard total shoulder arthroplasty or a reverse shoulder arthroplasty. In this example, details of the virtual surgical plan may include details relating to at least one of preparation of glenoid bone or preparation of humeral bone. In some examples, the orthopedic joint repair surgical procedure is one of a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, and an augmented glenoid reverse shoulder arthroplasty.

The virtual surgical plan may include a 3D virtual model corresponding to the anatomy of interest of the particular patient and a 3D model of a prosthetic component matched to the particular patient to repair the anatomy of interest or selected to repair the anatomy of interest. Furthermore, in the example of FIG. 2, the surgical planning system includes a storage system 206 to store data corresponding to the virtual surgical plan. The surgical planning system of FIG. 2 also includes MR system 212, which may comprise visualization device 213. In some examples, visualization device 213 is wearable by a user. In some examples, visualization device 213 is held by a user, or rests on a surface in a place accessible to the user. MR system 212 may be configured to present a user interface via visualization device 213. The user interface is visually perceptible to the user using visualization device 213. For instance, in one example, a screen of visualization device 213 may display real-world images and the user interface on a screen. In some examples, visualization device 213 may project virtual, holographic images onto see-through holographic lenses and also permit a user to see real-world objects of a real-world environment through the lenses. In other words, visualization device 213 may comprise one or more see-through holographic lenses and one or more display devices that present imagery to the user via the holographic lenses to present the user interface to the user.

In some examples, visualization device 213 is configured such that the user can manipulate the user interface (which is visually perceptible to the user when the user is wearing or otherwise using visualization device 213) to request and view details of the virtual surgical plan for the particular patient, including a 3D virtual model of the anatomy of interest (e.g., a 3D virtual bone of the anatomy of interest) and a 3D model of the prosthetic component selected to repair an anatomy of interest. In some such examples, visualization device 213 is configured such that the user can manipulate the user interface so that the user can view the virtual surgical plan intraoperatively, including (at least in some examples) the 3D virtual model of the anatomy of interest (e.g., a 3D virtual bone of the anatomy of interest). In some examples, MR system 212 can be operated in an augmented surgery mode in which the user can manipulate the user interface intraoperatively so that the user can visually perceive details of the virtual surgical plan projected in a real environment, e.g., on a real anatomy of interest of the particular patient. In this disclosure, the terms real and real world may be used in a similar manner. For example, MR system 212 may present one or more virtual objects that provide guidance for preparation of a bone surface and placement of a prosthetic implant on the bone surface. Visualization device 213 may present one or more virtual objects in a manner in which the virtual objects appear to be overlaid on an actual, real anatomical object of the patient, within a real-world environment, e.g., by displaying the virtual object(s) with actual, real-world patient anatomy viewed by the user through holographic lenses. For example, the virtual objects may be 3D virtual objects that appear to reside within the real-world environment with the actual, real anatomical object.

As described above, in some examples, the techniques described in this disclosure further provide for ways in which to determine whether bone can be extracted from a donor site for grafting. For example, in orthopedics, autograft is commonly used for bony reconstruction. Surgeons extract a bone graft from various locations within the patient's body according to volume and shape of the bone graft needed for the given bony reconstruction. However, the desired bone graft may be too large for a donor site and its extraction (e.g., harvesting) may lead to additional complications at the donor site such as bone fractures, cosmetic deformities, injuries to surrounding tissue, and the like.

As an example, in reverse shoulder arthroplasty, a bone graft is extracted from the humeral head (e.g., the humeral head is the donor site) and used to augment or reconstruct the glenoid bone (e.g., for preparation to insert prothesis). This technique is referred to as BIO-RSA (bony increased offset-reverse shoulder arthroplasty). If the bone graft extracted from the humeral head is too large, there may be possibility that the extraction results in fracture of the tuberosities, rotator cuff injury and/or excessive bone removal that may alter the quality of the fixation of the component for the BIO-RSA (e.g., stem or nucleus inserted into the humerus).

In accordance with one or more examples described in this disclosure, preoperative surgical planning system 202 may be configured to retrieve image data for one or more images of anatomical objects stored in storage system 206. The images of the anatomical objects include representations (e.g., as image data) of anatomical objects such as a first anatomical object (e.g., diseased bone) and a second anatomical object (e.g., donor site).

Preoperative surgical planning system 202 may determine a bone graft template for a bone graft to be connected to the first anatomical object. For example, visualization device 213 may display a representation of the first anatomical object. The surgeon, viewing the representation of the first anatomical object, may determine the size and shape of the bone graft that is to be connected to the first anatomical object. The surgeon may interact with the displayed representation and draw a bone graft template based on the size and shape of the bone graft. Visualization device 213 may display the bone graft template with the first anatomical object for the surgeon to confirm that the bone graft template adequately represents the bone graft that is to be connected.

Processing device(s) 210 may output information of the bone graft template to preoperative surgical planning system 202. This is one example way in which preoperative surgical planning system 202 may determine the bone graft template.

In some examples, storage system 206 may store a plurality of pre-generated bone graft templates of various size and shapes. Visualization device 213 may display the pre-generated bone graft templates, and the surgeon may select one of the pre-generated bone graft templates. Processing device(s) 210 may output information of the selected pre-generated bone graft template to preoperative surgical planning system 202. This is another example way in which preoperative surgical planning system 202 may determine the bone graft template.

In some examples, preoperative surgical planning system 202 may be configured to determine the bone graft template for the bone graft, and possibly with little to no intervention from the surgeon. For example, preoperative surgical planning system 202 may be configured to determine a shape of the first anatomical object. There may be various ways in which preoperative surgical planning system 202 may determine the shape of the first anatomical object, such as by segmenting out the first anatomical object from the other anatomical objects. Example ways in which to segment out the first anatomical object are described in U.S. Provisional Application Ser. Nos. 62/826,119, 62/826,133, 62/826,146, 62/826,168, and 62/826,190 all filed on Mar. 29, 2019 and incorporated by reference in their entirety. There may be other example ways in which to segment out the first anatomical object, such as in U.S. Pat. No. 8,971,606, and incorporated by reference in its entirety.

As one example, for segmenting, preoperative surgical planning system 202 may utilize differences in voxel intensities in image data to identify separation between bony regions and tissue regions to identify the first anatomical object. As another example, for segmenting, preoperative surgical planning system 202 may utilize closed-surface fitting (CSF) techniques in which preoperative surgical planning system 202 uses a shape model (e.g., predetermined shape like a sphere or a shape based on statistical shape modeling) and expands or constricts the shape model to fit a contour used to identify separation locations between bony regions and tissue or between tissue.

Preoperative surgical planning system 202 may determine a pre-morbid shape of the target bone (e.g., prior to disease or damage in examples where the target bone is for diseased or damaged bone) of the first anatomical object. Example ways in which to determine the pre-morbid shape of the first anatomical object are described in U.S. Provisional Application Nos. 62/826,172, 62/826,362, and 62/826,410 all filed on Mar. 29, 2019, and incorporated by reference in their entirety.

As one example, for determining pre-morbid shape, preoperative surgical planning system 202 may align a representation of the first anatomical object to coordinates of an SSM of the first anatomical object. Preoperative surgical planning system 202 may deform the SSM to determine an SSM that registers to the representation of the aligned first anatomical object. The version of the SSM that registers to the representation of the first anatomical object may be the pre-morbid shape of the target bone.

Preoperative surgical planning system 202 may compare the shape of the first anatomical object to the pre-morbid shape of the first anatomical object. For example, preoperative surgical planning system 202 may determine a difference between the first anatomical object (e.g., how the first anatomical object appears after disease or damage) and the pre-morbid shape of the first anatomical object (e.g. how the first anatomical object appeared before disease or damage). Based on the comparison (e.g., difference), preoperative surgical planning system 202 may determine the bone graft template. For instance, preoperative surgical planning system 202 may determine a bone graft template that has the approximately the same size and shape as the difference between the shape of the first anatomical object and the pre-morbid shape of the first anatomical object.

In one or more examples, preoperative surgical planning system 202 may be configured to determine information indicative of placement of the bone graft template within a representation of a second anatomical object (e.g., donor site) based on the image data. For example, the image data includes representations of various anatomical objects within the patient, such as the humeral head and the humerus, the iliac crest, and the like. Using BLUEPRINT™ or using one or more the segmentation techniques described in U.S. Provisional Application Ser. Nos. 62/826,119, 62/826,133, 62/826,146, 62/826,168, and 62/826,190 all filed on Mar. 29, 2019 or U.S. Pat. No. 8,971,606, visualization device 213 may display a representation of the second anatomical object (e.g., a 3D representation of a potential donor site). Although described with respect to a 3D representation, in some examples, visualization device 213 may display 2D scans of the second anatomical object.

Using visualization device 213, the surgeon may "drag and drop" the bone graft template (e.g., as drawn by the surgeon or as determined by preoperative surgical planning system 202) include the representation of the second anatomical object. In some examples, the surgeon may translate or rotate the bone graft template along the x, y, and/or z axis before or after dragging and dropping the bone graft template in the representation of the second anatomical object.

In some examples, preoperative surgical planning system 202 may be configured to perform the calculations of rotating the bone graft template and calculating the coordinates of the bone graft template for aligning the bone graft template to the coordinate space of the representation of the second anatomical object. For example, the bone graft template and the representation of the second anatomical object may be in different coordinate systems, and to move the bone graft template to the representation of the second anatomical object (e.g., donor site), preoperative surgical planning system 202 may determine a transformation matrix that provides for rotation, translation, scaling, and shearing, as needed so that the bone graft template and the second anatomical object are in the same coordinate system. One example way in which preoperative surgical planning system 202 may perform the rotation, translation, scaling, and shearing is using the OpenGL application programming interface (API); however, other ways in which to perform the rotation, translation, scaling, and shearing are possible. Also, once the bone graft template is in the coordinate system of the second anatomical object or before the bone graft template is in the coordinate system of the second anatomical object, the surgeon may rotate the bone graft template to view the bone graft template from different perspectives. Preoperative surgical planning system 202 performing the above example operations of aligning coordinate system, rotating, and moving the bone graft template into the representation of the second anatomical object are non-limiting examples of preoperative surgical planning system 202 determining information indicative of a placement of the bone graft template within a representation of the second anatomical object based on the image data.

In the above example of preoperative surgical planning system 202 determining information indicative of a placement of the bone graft template within a representation of the second anatomical object based on the image data, the surgeon performed "dragging and dropping" operations. In some examples, preoperative surgical planning system 202 may be configured to determine information indicative of placement of the bone graft template within a representation of the second anatomical object based on the image data with little to no intervention from the surgeon.

For example, preoperative surgical planning system 202 may align the bone graft template to the coordinate system of the second anatomical object. Preoperative surgical planning system 202 may then, based on the coordinates of the bone graft template (e.g., coordinates along the boundary of the bone graft template) and coordinates of the second anatomical object, move the bone graft template to be within the representation of the second anatomical object. For instance, preoperative surgical planning system 202 may rotate and shift the bone graft template so that the bone graft template fits within the representation of the second anatomical object.

Accordingly, preoperative surgical planning system 202 may compare a size and shape of the bone graft template to the representation of the second anatomical object and determine information indicative of the placement based on the comparison. In this manner, preoperative surgical planning system 202 may determine information indicative of placement of the bone graft template within a representation of the second anatomical object based on the image data.

In the above examples, the bone graft template is described as being aligned with the coordinate system of the second anatomical object. In some examples, the second anatomical object may be aligned with the coordinate system of the bone graft template.

In some examples, preoperative surgical planning system 202 may be configured with criteria that preoperative surgical planning system 202 uses when determining information indicative of placement of the bone graft template within the representation of the second anatomical object. For example, preoperative surgical planning system 202 may be configured to determine bone density of the second anatomical object such as based on U.S. Provisional Application No. 62/826,168 filed Mar. 29, 2019. If the bone density is too low (e.g., below a threshold) in certain portions, preoperative surgical planning system 202 may not determine whether the bone graft template can be placed in the portions having low bone density.

As another example, preoperative surgical planning system 202 may determine whether a particular placement of the bone graft template would cause the bone graft template to cross a cortical wall within the second anatomical object. If the particular placement would cause the bone graft template to cross the cortical wall, then preoperative surgical planning system 202 may determine that the particular placement is not a valid placement of the bone graft template.

As another example, preoperative surgical planning system 202 may determine whether a particular placement of the bone graft template would result in complicated surgery, preoperative surgical planning system 202 may determine that the particular placement is not a valid placement of the bone graft template. For example, if placement of the bone graft template in a particular location would result in the bone graft not being accessible or require complicated surgery (e.g., excessive shifting of bone, higher changes of complication, etc.) to access the bone graft, then preoperative surgical planning system 202 may determine that the such placement of the bone graft template is not valid.

There may be other criteria that preoperative surgical planning system 202 may utilize when determining information indicative of placement of the bone graft template within the representation of the second anatomical object. Preoperative surgical planning system 202 may be configured to use the above examples of the criteria and the additional examples of the criteria either alone or in any combination.

In some examples, preoperative surgical planning system 202 may be configured to output information indicative of whether the second anatomical object is potentially suitable as a donor site for the bone graft. For example, preoperative surgical planning system 202 may utilize the various criteria to determine whether the bone graft template can be placed in the second anatomical object. If there are no valid placements for the bone graft template, preoperative surgical planning system 202 may output information indicating that the second anatomical object may not be suitable as a donor site. If there are valid placements for the bone graft template, preoperative surgical planning system 202 may output information indicating that the second anatomical object is suitable as a donor site.

In some examples, there may be multiple ways in which the bone graft template can fit within the second anatomical object. Preoperative surgical planning system 202 may output the various valid options indicating from where the bone graft can be extracted from the second anatomical object. In some examples, preoperative surgical planning system 202 may rank the valid options. In some examples, preoperative surgical planning system 202 may determine the best of the valid options (e.g., the location within the second anatomical object from where the bone graft can be removed with the greatest ease while minimizing impact to patient).

Preoperative surgical planning system 202 may be configured to output information indicative of the placement of the bone graft template within the representation of the second anatomical object. As one example, preoperative surgical planning system 202 may generate information used by visualization device 213 to render the bone graft template within the representation of the second anatomical object at the determined placement. As another example, preoperative surgical planning system 202 may generate coordinate values of the location of the bone graft template. There may be other examples of the information that preoperative surgical planning system 202 generates for outputting that is indicative of the placement of the bone graft template within the representation of the second anatomical object (e.g., donor site).

In some examples, preoperative surgical planning system 202 may be configured to generate pre-operative planning information based on placement of the bone graft template within the representation of the second anatomical object. For example, the information indicative of the placement of the bone graft template may include information indicative of where the bone graft template is located within the representation of the second anatomical object. The bone graft template may therefore provide a visual indication of from where to extract the bone graft.

As one example, preoperative surgical planning system 202 may be configured to generate information indicative of a location within the second anatomical object from which the bone graft is to be extracted (e.g., that is to be cut for extracting the bone graft). Visualization device 213 may display the location that is to be cut for extracting the bone graft. Visualization device 213 may display the location preoperatively and/or intraoperatively.

As one example, preoperative surgical planning system 202 may be configured to generate information indicative of an axis along which to the second anatomical object for extracting the bone graft. Visualization device 213 may display the axis that is to be cut for extracting the bone graft. Visualization device 213 may display the axis preoperatively and/or intraoperatively.

As one example, preoperative surgical planning system 202 may be configured to generate information indicative of a maximum depth at which to cut the second anatomical object for extracting the bone graft. Visualization device 213 may display the maximum depth preoperatively and/or intraoperatively.

As one example, preoperative surgical planning system 202 may be configured to generate information indicative of a types of tool to utilize to cut the second anatomical object for extracting the bone graft. Visualization device 213 may display the types of tools preoperatively and/or intraoperatively 1.

In the above examples, preoperative surgical planning system 202 is described as performing various operations. In some examples, the operations of preoperative surgical planning system 202 may be performed by processing device(s) 210. In some examples, some of the example operations described above may be performed by preoperative surgical planning system 202 and some of the example operations described above may be performed by processing device(s) 210.

In this disclosure, processing circuitry may be considered as performing example operations described in this disclosure. The processing circuitry may be processing circuitry of preoperative surgical planning system 202 or may be processing device(s) 210. In some examples, the processing circuitry refers to the processing circuitry distributed between MR system 212 and preoperative surgical planning system 202, as well as other processing circuitry in system 200.

Figure 3:
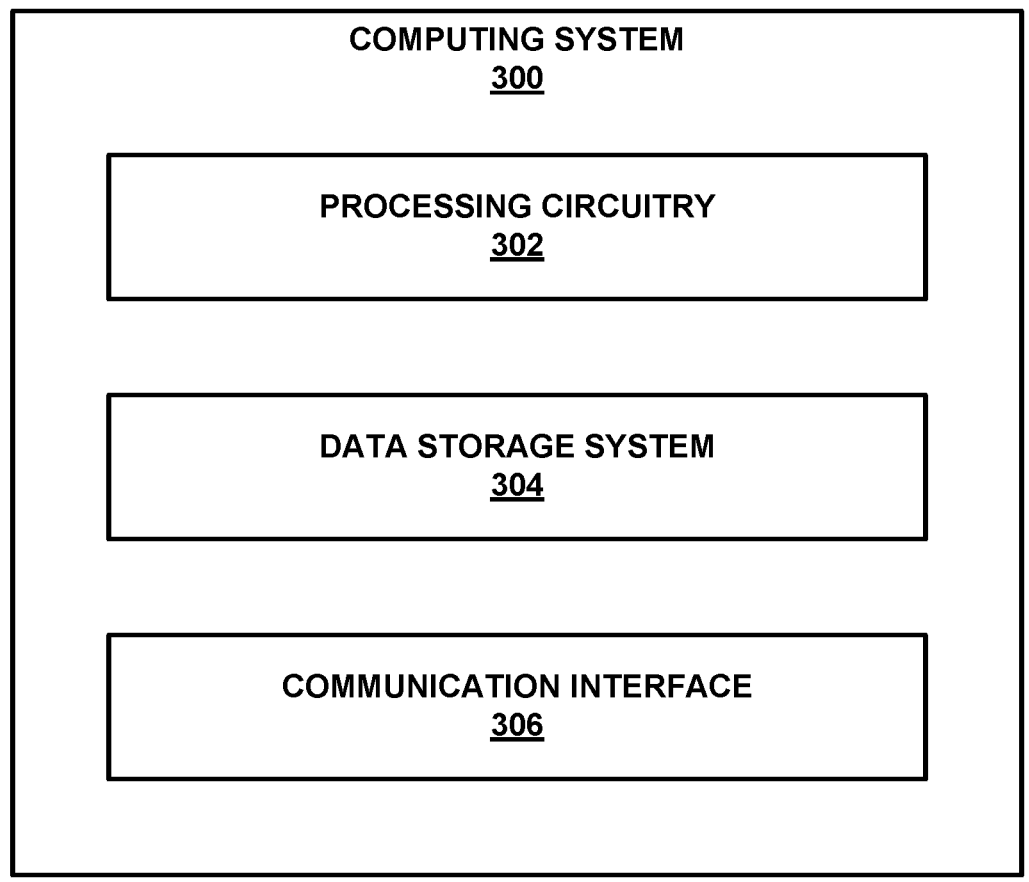
FIG. 3 is a block diagram illustrating an example of computing system configured to perform one or more examples described in this disclosure.

FIG. 3 is a block diagram illustrating an example of computing system configured to perform one or more examples described in this disclosure. FIG. 3 illustrates an example of computing system 300, and preoperative surgical planning system 202 is an example of computing system 300. Examples of computing system 300 include various types of computing devices, such as server computers, personal computers, smartphones, laptop computers, and other types of computing devices.

Computing system 300 includes processing circuitry 320, data storage system 304, and communication interface 306. Computing system 300 may include additional components, such as a display, keyboard, etc., not shown in FIG. 3 for ease. Also, in some examples, computing system 300 may include fewer components. For example, data storage system 304 may be similar to storage system 206 of FIG. 2 and reside off of (e.g., be external to) computing system 300. However, data storage system 304 may be part of computing system 300 as illustrated. Even in examples where data storage system 304 is external to computing system 300, computing system 300 may still include local memory for storing instructions for execution by processing circuitry 302 and provide functionality for storing data used by or generated by processing circuitry 302. When data storage system 304 is the local memory, the amount of storage provided by data storage system 304 may less than storage system 206.

Examples of processing circuitry 302 include fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable.

Examples of data storage system 304 include RAM, ROM, EEPROM, CD-ROM or other optical disk storage, magnetic disk storage, or other magnetic storage devices, flash memory, or any other medium that can be used to store data. In some examples, data storage system 304 may also store program code in the form of instructions or data structures and that can be accessed by processing circuitry 302 for execution.

Communication interface 306 refers to circuitry that allows computing system 300 to connect, wirelessly or with wired connection, with other components. For instance, communication interface 306 provides the circuitry that allows computing device 300 to transmit to and receive from network 208 of FIG. 2.

Processing circuitry 302 is an example of processing circuitry configured to perform one or more example techniques described in this disclosure. In some examples, such as where MR system 212 is configured to perform various operations of preoperative surgical planning system 202, processing device(s) 210 may include processing circuitry 302. Also, in some examples, the processing circuitry that is configured to perform the example operations described in this disclosure may include the combination of processing circuitry 302, processing device(s) 210, and possibly one or more other processing circuitry. For example, FIG. 3 is described with respect to processing circuitry 302.

For example, data storage system 304 may store image data for one or more images of anatomical objects, and processing circuitry 302 may access the image data from data storage system 304. Utilizing one or more of the example techniques described above, processing circuitry 302 may be configured to determine a bone graft template for a bone graft to be connected to a first anatomical object, determine information indicative of placement of the bone graft template within a representation of a second anatomical object based on the image data, and output the information indicative of the placement of the bone graft template within the representation of the second anatomical object.

Figure 4:
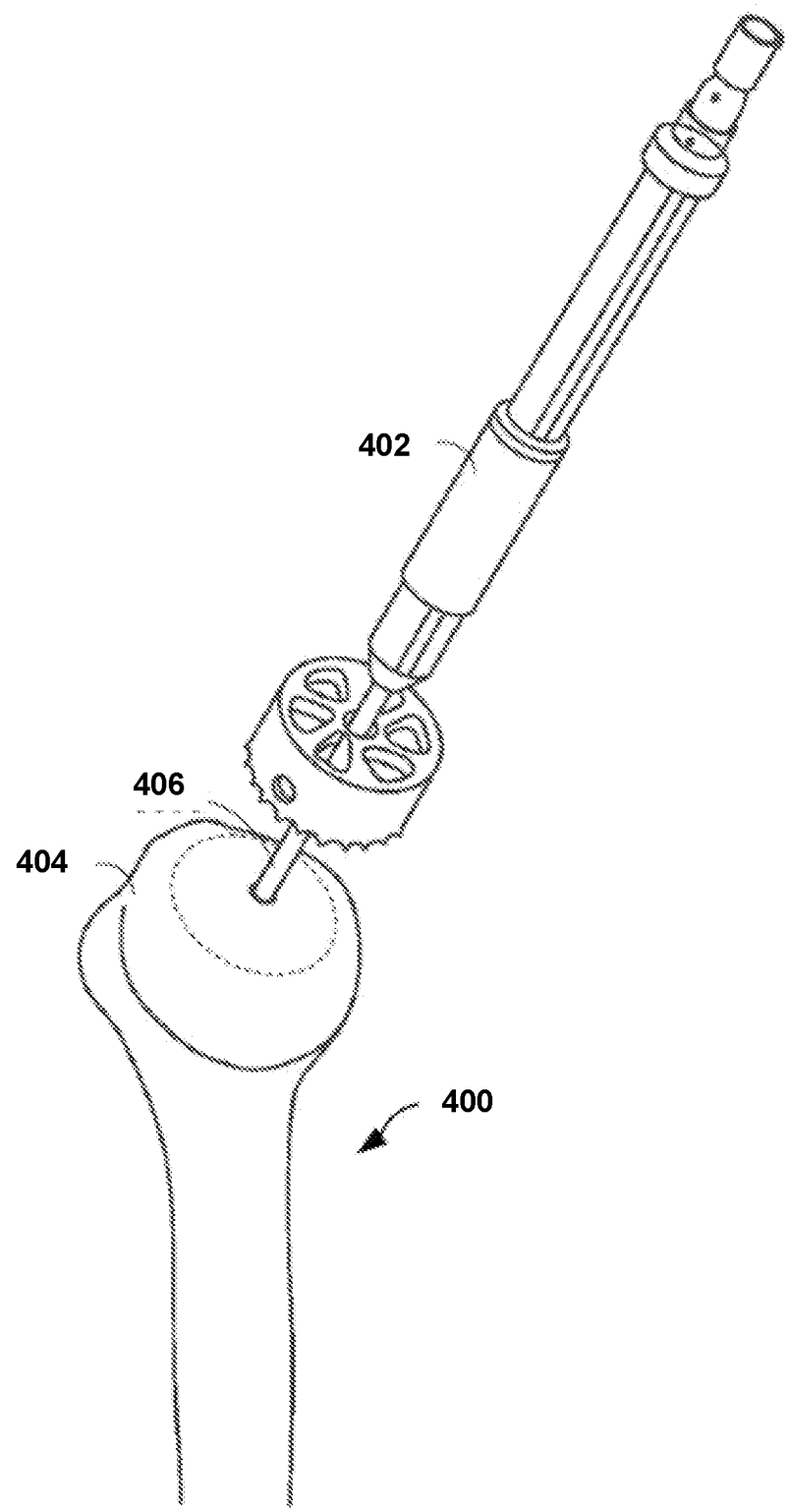
FIGS. 4 and 5 are conceptual diagrams illustrating examples of bone extraction for bone grafting.
Figure 5:
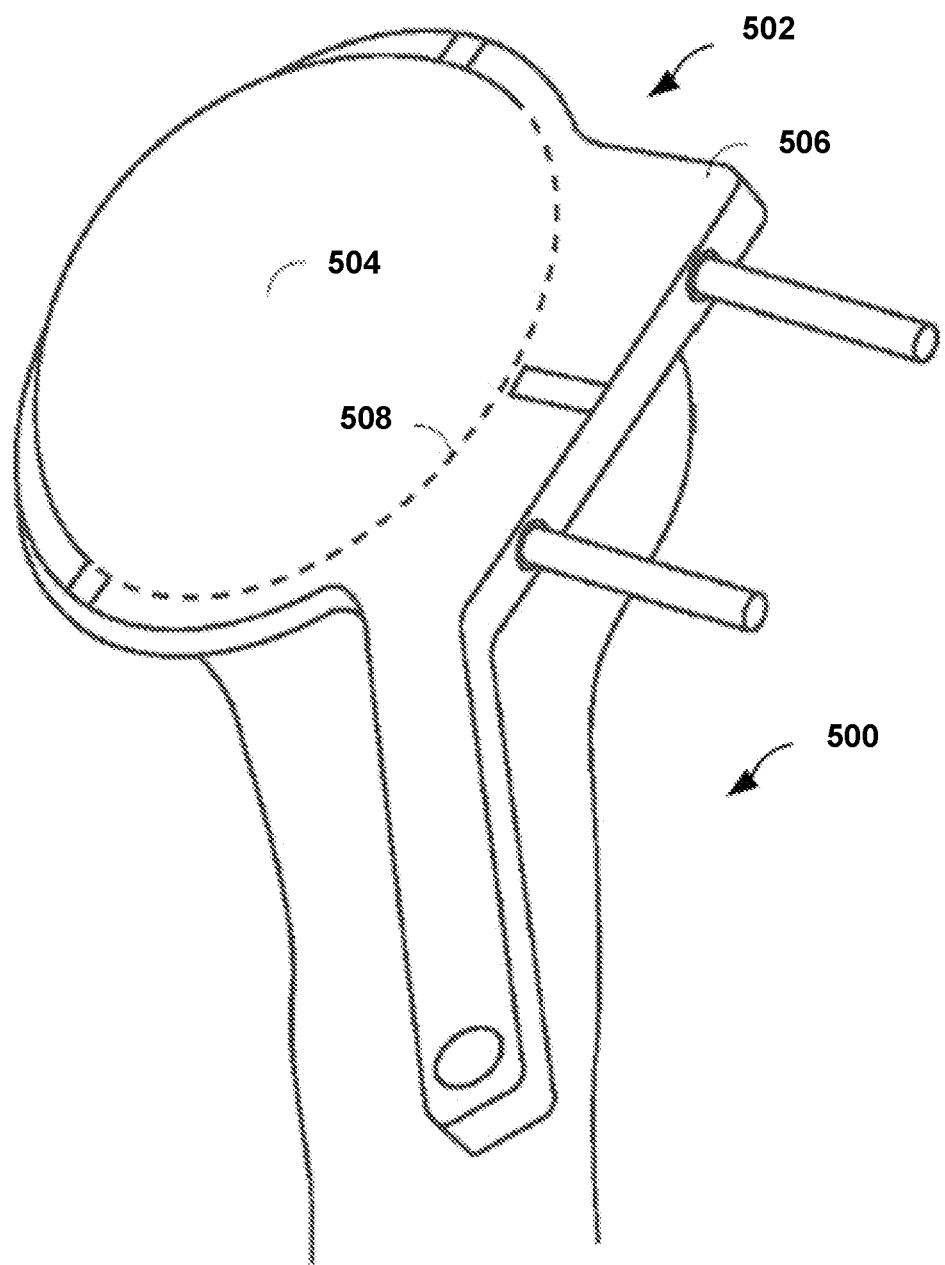

FIGS. 4 and 5 are conceptual diagrams illustrating examples of bone extraction for bone grafting. For example, FIGS. 4 and 5 illustrate examples of bone extraction (e.g., harvesting) for bony increased offset-reverse shoulder arthroplasty (BIO-RSA). Other example procedures that may utilize the techniques described in this disclosure include the Norris technique. One example of the Norris technique is available from Norris, Tom & Kelly, James & Humphrey, C. (2007). "Management of Glenoid Bone Defects in Revision Shoulder Arthroplasty: A New Application of the Reverse Total Shoulder Prosthesis." Techniques in Shoulder & Elbow Surgery. 8. 37-46. 10.1097/BTE.0b013e318030d3b7.

As shown in FIG. 4, graft reaming tool 402 may be used to ream the surface of humeral head 404 of humerus 400. The surgeon may connect graft reaming tool 402 to a drill or other instrument and MR system 212 may display virtual guidance to assist in reaming the surface of humeral head 404. For instance, MR system 212 may display depth guidance to enable the surgeon to ream the surface of humeral head 404 to a target depth. As another example, MR system 212 may provide targeting guidance. For instance, MR system 212 may display one or both of a virtual marker that identifies a center point or prescribed axis of the reaming and/or an indication of whether graft reaming tool 402 is aligned with the prescribed axis.

In this example, graft reaming tool 402 may be a cannulated reaming tool configured to be positioned and/or guided by a guide pin, such as guide 406. In other examples, graft reaming tool 402 may not be cannulated and may be guided without the assistance of a physical guide pin. For instance, MR system 212 may provide virtual guidance (e.g., depth guidance and/or targeting guidance such as a displayed virtual marker) to enable a surgeon to ream a graft from humeral head 404 without the use of guide 406.

As shown in FIG. 5, a surgeon may attach mechanical guide 502 on humerus 500 prior to performing a resection of humeral head 504. The surgeon may adjust one or more components of mechanical guide 502 such that top surface 506 of mechanical guide 502 is co-planar with anatomic neck 508 of humerus 500 (for purposes of illustration, anatomic neck 508 is illustrated as a broken line). After attaching mechanical guide 502 to humeral head 504 and adjusting the mechanical guide, the surgeon may perform the resection of humeral head 504 by guiding a cutting tool (e.g., a blade of an oscillating saw) along top surface 506.

Figure 6:
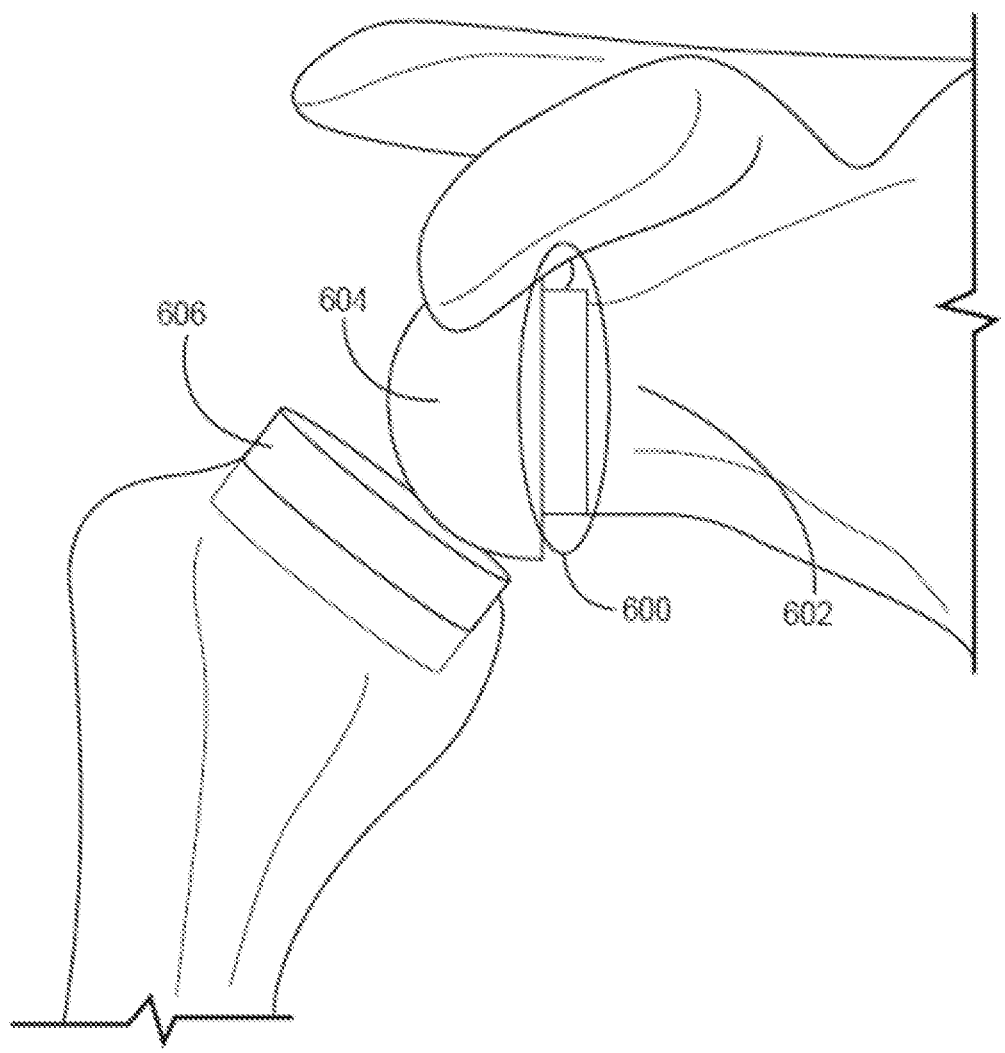
FIG. 6 is a conceptual diagram illustrating an example of the extracted bone grafted to glenoid bone.

FIG. 6 is a conceptual diagram illustrating an example of the extracted bone grafted to glenoid bone. As shown in FIG. 6, bone graft 600, possibly taken from humeral head 404 (FIG. 4) or 504 (FIG. 5), is grafted to glenoid 602. Stem 606 of prosthesis 604 is inserted into bone graft 600, as part of the BIO-RSA. Stem 606, with bone graft 600, is inserted into the humerus, as part of the BIO-RSA.

Figure 7A:
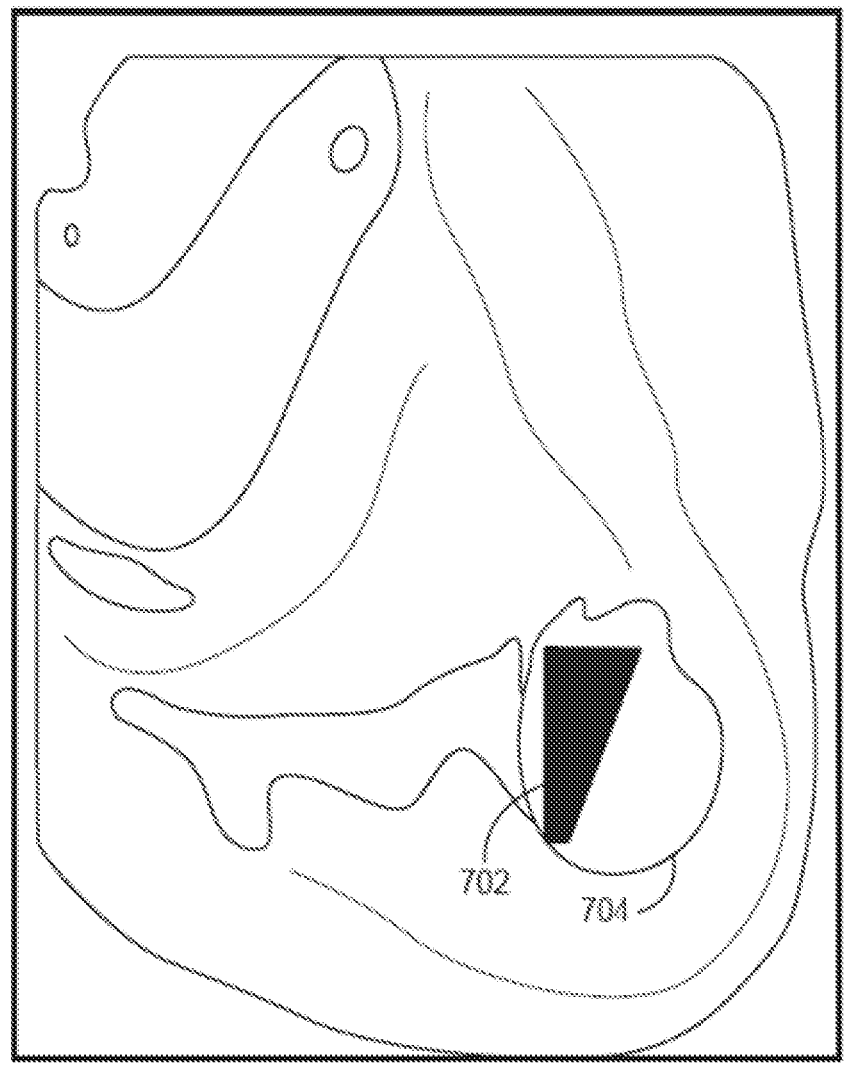
FIGS. 7A and 7B are conceptual diagrams illustrating examples of a bone graft template within a representation of a donor site.
Figure 7B:
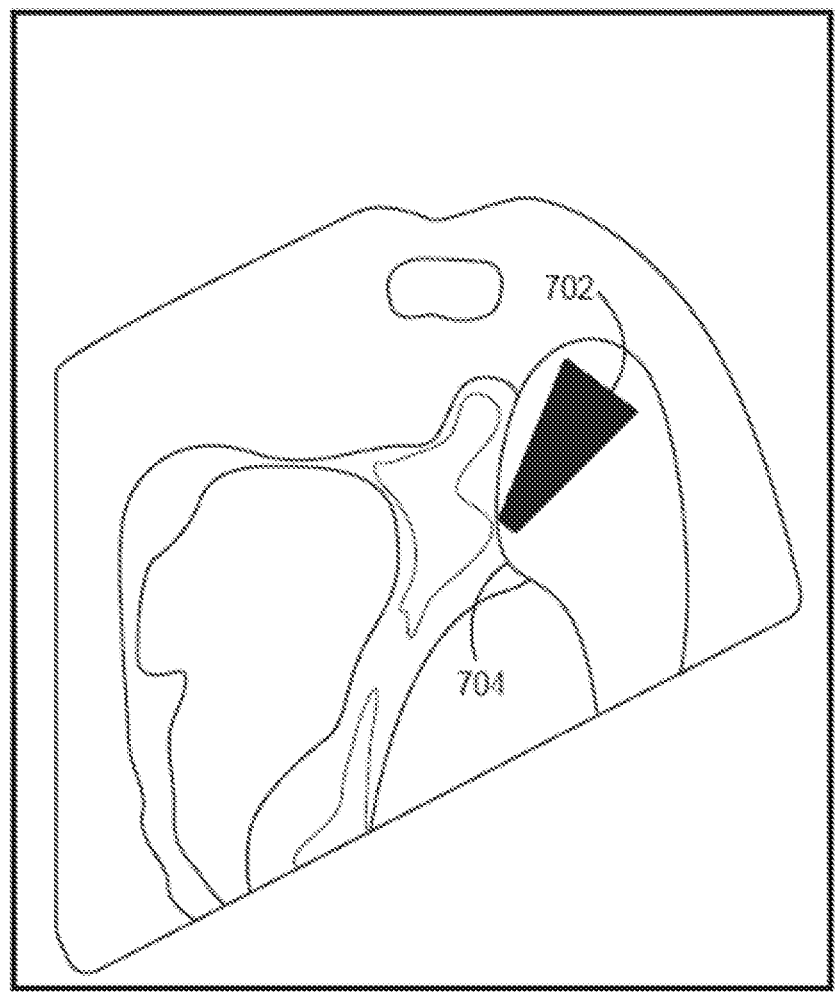

FIGS. 7A and 7B are conceptual diagrams illustrating examples of a bone graft template within a representation of a donor site. FIGS. 7A and 7B illustrate bone graft template 702 and donor site (e.g., humeral head) 704. For ease of illustration, bone graft template 702 and donor site 704 is illustrated as two-dimensional images. Visualization device 213 may be configured to display bone graft template 702 and donor site 704 as three-dimensional images. However, visualization device 213 may display bone graft template 702 and donor site 704 in two-dimensional images, such as images from different perspectives.

Processing circuitry (e.g., processing circuitry 302, processing device(s) 210, or a combination thereof) may be configured to determine bone graft template 702 for a bone graft to be connected to a first anatomical object (e.g., glenoid bone 602 of FIG. 6). The processing circuitry may utilize the various example techniques described above to determine bone graft template 702. The processing circuitry may be configured to determine information indicative of placement of bone graft template 702 within a representation of a second anatomical object (e.g., donor site 704) based on the image data utilizing the above example techniques.

The processing circuitry may output information indicative of the placement of bone graft template 702 within the representation of the second anatomical object (e.g., donor site 704). For example, FIGS. 7A and 7B illustrate the rendering of bone graft template 702 within donor site 704 from different perspectives. The graphical information used to render bone graft template 702 within donor site 704 is an example of the information that the processing circuitry outputs indicative of the placement of bone graft template 702 within donor site 704.

Figure 8:
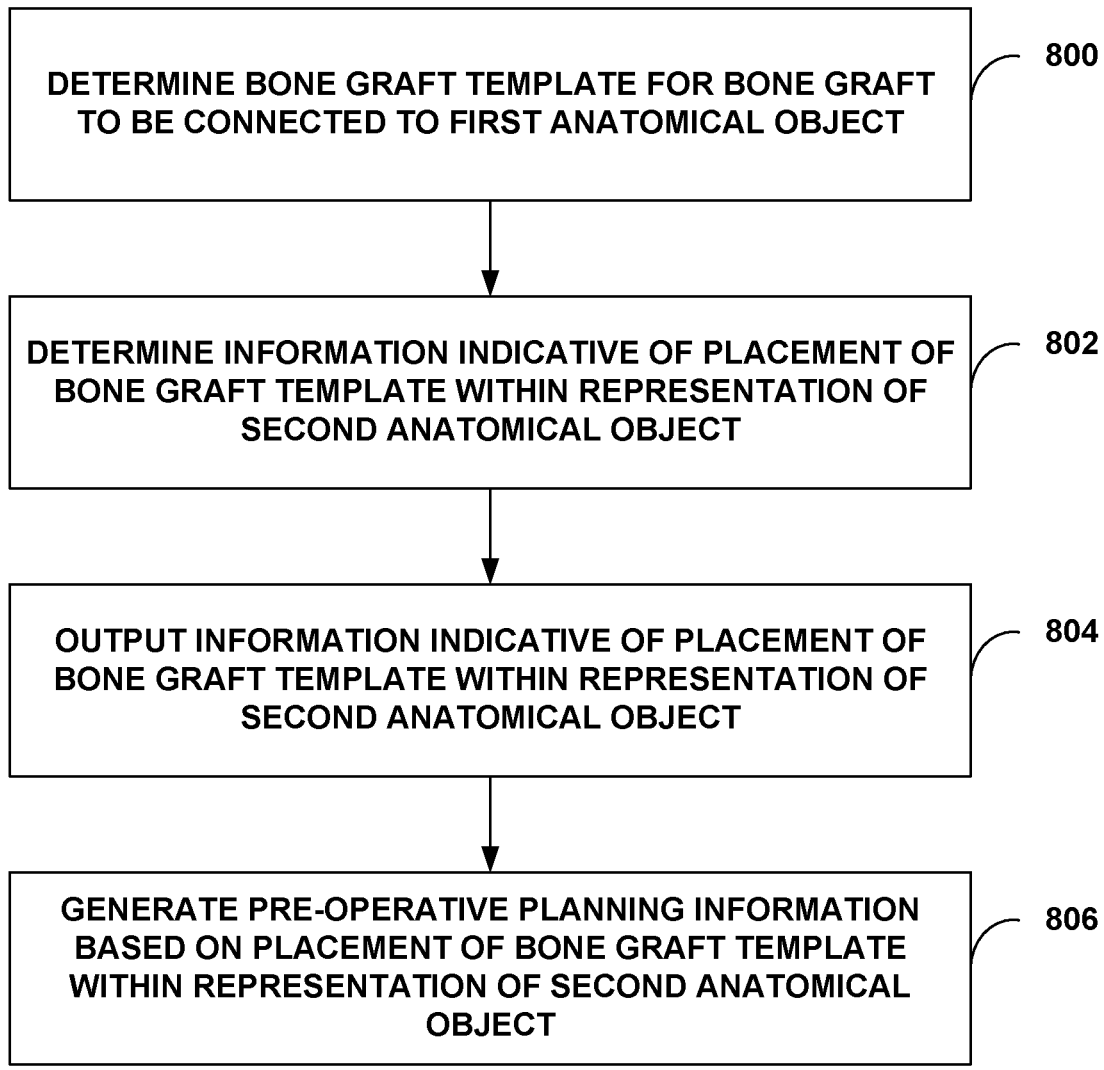
FIG. 8 is a flowchart illustrating example methods of operations in accordance with one or more example techniques described in this disclosure.

FIG. 8 is a flowchart illustrating example methods of operations in accordance with one or more example techniques described in this disclosure. The example techniques of FIG. 8 may be performed with processing circuitry (e.g., processing circuitry 302, processing device(s) 210, or a combination thereof).

The processing circuitry may determine a bone graft template for a bone graft to be connected to a first anatomical object (800). As one example, the processing circuitry may be configured to receive input of the bone graft template (e.g., based on drawing from surgeon or selection of pre-generated bone graft template). As another example, the processing circuitry may be configured to determine a shape of the first anatomical object, compare the shape of the first anatomical object to a pre-morbid shape of the first anatomical object, and determine the bone graft template based on the comparison.

The processing circuitry may determine information indicative of placement of the bone graft template within a representation of a second anatomical object based on stored image data (802). As one example, the processing circuitry may be configured to receive information indicative of placement of the bone graft template within the representation of the second anatomical object (e.g., based on "drag and drop" by surgeon). As one example, the processing circuitry may compare a size and shape of the bone graft template to the representation of the second anatomical object and determine information indicative of the placement based on the comparison.

The processing circuitry may output information indicative of the placement of the bone graft template within the representation of the second anatomical object (804). As one example, processing circuitry is configured to output graphical information for rendering, for display, the bone graft template within the representation of the second anatomical object. For instance, the processing circuitry may output graphical information for rendering, for display, the representation of the second anatomical object. In such examples, to receive information indicative of the placement of the bone graft template, the processing circuitry may be configured to receive information indicative of the placement of the bone graft template within the displayed representation of the second anatomical object. To output the information indicative of the placement of the bone graft, the processing circuitry may be configured to output graphical information for rendering, for display, the bone graft template within the displayed represented of the second anatomical object based on the received information indicative of the placement of the bone graft template within the displayed representation of the second anatomical object.

In some examples, the processing circuitry may be configured to output information indicative of whether the second anatomical object is potentially suitable as a donor site for the bone graft for the first anatomical object. For example, the processing circuitry may be configured with criteria to use to determine whether a placement of the bone graft template within the second anatomical object is valid. If the processing circuitry determines that there is no valid placement of the bone graft template in the second anatomical object, the processing circuitry may output information indicating that the second anatomical object is not suitable for a donor site for the bone graft for the first anatomical object.

The processing circuitry, may in some examples, recommend an alternative site when no valid placement of the bone graft is found. For example, the processing circuitry may be preloaded with representations of different possible second anatomical objects (e.g., humeral head, iliac crest, etc.). The processing circuitry may determine whether there are valid placements of the bone graft in the different second anatomical objects, and identify potential locations that can be candidates for the second anatomical object. Rather than trying different possible second anatomical objects, in some examples, the processing circuitry may determine valid placements in the different second anatomical objects and identify which ones of the second anatomical objects can be donor sites. The processing circuitry may also provide a ranking of second anatomical objects indicating which ones could be the best donor sites (e.g., in terms of ease of surgery and most available bone).

In some examples, the processing circuitry may generate pre-operative planning information based on placement of the bone graft template within the representation of the second anatomical object (806). As one example, the processing circuitry is configured to generate information indicative of a location within the second anatomical object from which the bone graft is to be extracted (e.g., that is to be cut for extracting the bone graft). As another example, the processing circuitry is configured to generate information indicative of an axis along which to the second anatomical object for extracting the bone graft. As another example, the processing circuitry is configured to generate information indicative of a maximum depth at which to cut the second anatomical object for extracting the bone graft. As another example, the processing circuitry is configured to generate information indicative of a types of tool to utilize to cut the second anatomical object for extracting the bone graft.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors or processing circuitry, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can be programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

The invention claimed is:

1. A system for orthopedic surgery, the system comprising:
   a memory configured to store image data for one or more images of a patient; and
   processing circuitry configured to:
   determine a bone graft template for a bone graft to be connected to a glenoid of the patient on which the bone graft is to be connected for implantation of an implant, the bone graft template being a graphical representation of a size and shape of the bone graft, wherein to determine the bone graft template, the processing circuitry is configured to:
determine a pre-morbid shape of the glenoid;
determine a shape of the glenoid;
compare the shape of the glenoid to the pre-morbid shape of the glenoid; and
determine the bone graft template based on the comparison;
determine placement of the bone graft template within a representation of a humeral head that is to be cut; and
output information indicative of the placement of the bone graft template within the representation of the humeral head.

2. The system of claim 1, wherein to determine the placement, the processing circuitry is configured to receive information indicative of the placement of the bone graft template within the representation of the humeral head, and wherein to output the information indicative of the placement, the processing circuitry is configured to output graphical information for rendering, for display, the bone graft template within the representation of the humeral head.

3. The system of claim 2, wherein the processing circuitry is configured to:
output graphical information for rendering, to display the representation of the humeral head,
wherein to receive the information indicative of the placement of the bone graft template, the processing circuitry is configured to receive the information indicative of the placement of the bone graft template within the displayed representation of the humeral head, and
wherein to output the information indicative of the placement of the bone graft template, the processing circuitry is configured to output graphical information for rendering, for display, the bone graft template within the displayed representation of the humeral head based on the received information indicative of the placement of the bone graft template within the displayed representation of the humeral head.

4. The system of claim 1,
wherein to determine the placement of the bone graft template, the processing circuitry is configured to:
compare a size and shape of the bone graft template to the representation of the humeral head; and
determine the placement of the bone graft template based on the comparison of the size and shape of the graft template to the representation of the humeral head, and
wherein to output the information indicative of the placement of the bone graft template, the processing circuitry is configured to output graphical information for rendering, for display, the bone graft template within the representation of the humeral head.

5. The system of claim 1, wherein the processing circuitry is configured to output information indicative of whether the humeral head is potentially suitable as a donor site for the bone graft.

6. The system of claim 1, wherein the processing circuitry is configured to generate pre-operative planning information based on the placement of the bone graft template within the representation of the humeral head.

7. The system of claim 6, wherein to generate the pre-operative planning information, the processing circuitry is configured to generate information indicative of a location within the humeral head from which the bone graft is to be extracted.

8. The system of claim 6, wherein to generate the pre-operative planning information, the processing circuitry is configured to generate information indicative of an axis along which to cut the humeral head for extracting the bone graft.

9. The system of claim 6, wherein to generate the pre-operative planning information, the processing circuitry is configured to generate information indicative of a maximum depth at which to cut the humeral head for extracting the bone graft.

10. The system of claim 6, wherein to generate the pre-operative planning information, the processing circuitry is configured to generate information indicative of a type of tool to utilize to cut the humeral head for extracting the bone graft.

11. A method for bone graft selection in orthopedic surgery, the method comprising:
determining a bone graft template for a bone graft to be connected to a glenoid of a patient on which the bone graft is to be connected for implantation of an implant, the bone graft template being a graphical representation of a size and shape of the bone graft, wherein determining the bone graft template comprises:
determining a pre-morbid shape of the glenoid;
determining a shape of the glenoid;
comparing the shape of the glenoid to the pre-morbid shape of the glenoid; and
determining the bone graft template based on the comparison;
determining placement of the bone graft template within a representation of a humeral head that is to be cut; and
outputting information indicative of the placement of the bone graft template within the representation of the humeral head.

12. The method of claim 11, wherein determining the placement comprises receiving the information indicative of the placement of the bone graft template within the representation of the humeral head, and outputting the information indicative of the placement comprises outputting graphical information for rendering, for display, the bone graft template within the representation of the humeral head.

13. The method of claim 12, further comprising:
outputting graphical information for rendering, to display the representation of the humeral head,
wherein receiving the information indicative of the placement of the bone graft template comprises receiving the information indicative of the placement of the bone graft template within the displayed representation of the humeral head, and
outputting the information indicative of the placement of the bone graft template comprises outputting graphical information for rendering, for display, the bone graft template within the displayed representation of the humeral head based on the received information indicative of the placement of the bone graft template within the displayed representation of the humeral head.

14. The method of claim 11,
wherein determining the placement of the bone graft template comprises:
comparing a size and shape of the bone graft template to the representation of the humeral head; and
determining information indicative of the placement of the bone graft template based on the comparison of the size and shape of the graft template to the representation of the humeral head, and wherein outputting the information indicative of the placement of the bone graft template comprises outputting graphical information for rendering, for display, the bone graft template within the representation of the humeral head.

15. The method of claim 11, further comprising outputting information indicative of whether the humeral head is potentially suitable as a donor site for the bone graft.

16. The method of claim 11, further comprising generating pre-operative planning information based on the placement of the bone graft template within the representation of the humeral head.

17. The method of claim 16, wherein generating the pre-operative planning information comprises generating information indicative of a location within the humeral head from which the bone graft is to be extracted.

18. The method of claim 16, wherein generating the pre-operative planning information comprises generating information indicative of an axis along which to cut the humeral head for extracting the bone graft.

19. The method of claim 16, wherein generating the pre-operative planning information comprises generating information indicative of a maximum depth at which to cut the humeral head for extracting the bone graft.

20. The method of claim 16, wherein generating the pre-operative planning information comprises generating information indicative of a type of tool to utilize to cut the humeral head for extracting the bone graft.

21. A system for orthopedic surgery, the system comprising:
  means for determining a bone graft template for a bone graft to be connected to a glenoid of a patient on which the bone graft is to be connected for implantation of an implant, the bone graft template being a graphical representation of a size and shape of the bone graft, wherein the means for determining the bone graft template comprises means for:
    determining a pre-morbid shape of the glenoid;
    determining a shape of the glenoid;
    comparing the shape of the glenoid to the pre-morbid shape of the glenoid; and
    determining the bone graft template based on the comparison;
  means for determining placement of the bone graft template within a representation of a humeral head that is to be cut; and
  means for outputting information indicative of the placement of the bone graft template within the representation of the humeral head.

22. The system of claim 21, wherein the means for determining the placement of the bone graft template comprises:
  means for comparing a size and shape of the bone graft template to the representation of the humeral head; and
  means for determining the placement of the bone graft template based on the comparison, and
  wherein the means for outputting the information indicative of the placement of the bone graft template comprises means for outputting graphical information for rendering, for display, the bone graft template within the representation of the humeral head.

23. A non-transitory computer-readable storage medium storing instructions that when executed cause one or more processors to:
  determine a bone graft template for a bone graft to be connected to a glenoid of a patient on which the bone graft is to be connected for implantation of an implant, the bone graft template being a graphical representation of a size and shape of the bone graft, wherein the instructions that cause the one or more processors to determine the bone graft template comprise instructions that cause the one or more processors to:
    determine a pre-morbid shape of the glenoid;
    determine a shape of the glenoid;
    compare the shape of the glenoid to the pre-morbid shape of the glenoid; and
    determine the bone graft template based on the comparison
  determine placement of the bone graft template within a representation of a humeral head that is to be cut; and
  output information indicative of the placement of the bone graft template within the representation of the humeral head.

24. The non-transitory computer-readable storage medium of claim 23:
  wherein the instructions that cause the one or more processors to determine the placement of the bone graft template comprise instructions that cause the one or more processors to:
    compare a size and shape of the bone graft template to the representation of the humeral head; and
    determine the placement of the bone graft template based on the comparison of the size and shape of the graft template to the representation of the humeral head, and
  wherein the instructions that cause the one or more processors to output the information indicative of the placement of the bone graft template comprise instructions that cause the one or more processors to output graphical information for rendering, for display, the bone graft template within the representation of the humeral head.

* * * * *